United States Patent [19]

Heller

[11] Patent Number: 4,931,221

[45] Date of Patent: Jun. 5, 1990

[54] PHOTOCHROMIC SPIROPYRAN COMPOUNDS

[75] Inventor: Harry G. Heller, Cardiff, Wales

[73] Assignee: PPG Industries, Inc., Pittsburgh, Pa.

[21] Appl. No.: 292,599

[22] Filed: Dec. 30, 1988

[51] Int. Cl.$^5$ .................................................. G02B 5/23
[52] U.S. Cl. .................................. 252/586; 252/589; 549/381; 549/390; 549/389; 549/408; 549/406; 351/163; 350/354
[58] Field of Search ...................... 252/582, 589, 586; 549/408, 389, 390, 381, 406; 351/163; 350/354

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,886,184 | 5/1975 | Matsumoto et al. | 260/345.3 |
| 3,927,036 | 12/1975 | Lee | 260/345.3 |
| 4,051,152 | 9/1977 | Razdan et al. | 260/345.3 |
| 4,215,010 | 7/1980 | Hovey et al. | 252/300 |
| 4,238,501 | 12/1980 | Kabbe et al. | 424/283 |
| 4,342,668 | 8/1982 | Hovey et al. | 252/586 |
| 4,563,458 | 1/1986 | Widdig et al. | 514/253 |
| 4,637,698 | 1/1987 | Kwak et al. | 351/163 |

FOREIGN PATENT DOCUMENTS 246114 5/1987 European Pat. Off. .
250193 6/1987 European Pat. Off. .

OTHER PUBLICATIONS

Padwa et al, J. Org. Chem., vol. 40, No. 8, 1975, p. 1142.

Primary Examiner—Matthew A. Thexton
Assistant Examiner—Richard Treanor
Attorney, Agent, or Firm—Irwin M. Stein

[57] ABSTRACT

Described are a series of novel photochromic benzopyran and naphthopyran compounds in which two cyclopropyl groups are appended at the 2-position of the benzopyran or naphthopyran ring. Also described are organic host materials that contain or that are coated with such compounds. Articles such as ophthalmic or plano lenses that incorporate the noval pyran compounds or combinations of the novel pyran compounds with other complementary photochromic compounds are described.

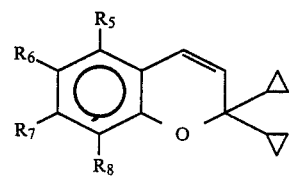

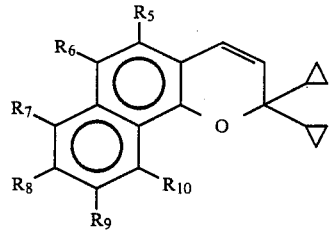

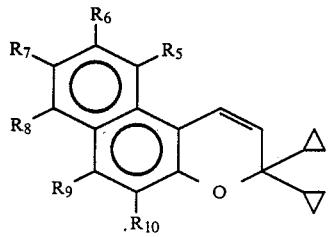

32 Claims, No Drawings

PHOTOCHROMIC SPIROPYRAN COMPOUNDS

DESCRIPTION OF THE INVENTION

The present invention relates to novel benzopyran and naphthopyran compounds, especially novel photochromic benzopyran and naphthopyran compounds, and to compositions and articles containing such novel pyran compounds. Photochromism is a reversible phenomenon exhibited by a compound which, when exposed to light radiation involving ultraviolet rays such as the ultraviolet radiation in sunlight or in the light of a mercury lamp, changes color and then returns to its original color if the ultraviolet radiation is discontinued or the compound is stored in the dark.

Various types of photochromic compounds have been synthesized and suggested for use in applications in which a color change or darkening is induced by sunlight. U.S. Pat. No. 3,567,605 (Becker) describes a series of pyran derivatives, including certain benzopyrans and naphthopyrans, which exhibit photochromic properties. These compounds are described as derivatives of chromene and are reported to undergo a color change, e.g., from colorless to yellow-orange on irradiation by ultraviolet light at temperatures below about minus 40° C. Irradiation of the compounds with visible light or upon raising the temperature in the range of −10° C. to 0° C. reverses the coloration to a colorless state. U.S. Pat. No. 4,563,458 describes certain 2H-chromenes as precursors of certain chroman-4-aldehydes, which are reacted with certain amines to prepare 4-aminomethylene-chromans and -chromenes that are used in medicaments.

European Patent Publication No. 246,114 describes a series of photochromic spiropyrans in which a spiroadamantane group is attached at the 2-position of the benzopyran or naphthopyran ring. European Patent Publication No. 250,193 describes photoreactive plastic lenses that are coated or impregnated with the photochromic spiropyrans of European Patent Publication No. 246,114 in combination with a blue photochromic benzopyran or naphthopyran having an aminophenyl substituent at the 2-position of the pyran ring.

Padwa et al in J. Org. Chem., Volume 40, No. 8, 1975, page 1142, describes his investigation of the photochemical reactions of compounds of the type described in U.S. Pat. No. 3,567,605 (Becker), identifies the by-products and suggests pathways to the ring-opened color intermediates and the final non-colored phenolics. The color forms examined by the authors are reported as being unstable at room temperature. The authors do not suggest ways in which the stability of the examined compounds might be improved, nor any modification that might be made to the structure of the known pyran compounds.

It has now been discovered that novel photochromic chromenes containing two cyclopropyl groups at the 2-position of the benzopyran or naphthopyran ring can be prepared. Preferred are the resulting naphthopyran compounds. The novel compounds of the present invention exhibit a deeper color and a larger bathochromic shift in the visible spectrum of the activated form compared to benzopyrans or naphthopyrans having alkyl groups attached at the 2-position of the pyran ring or a spirocycloalkyl group in the 2-position, such as the adamantylidene moiety.

DETAILED DESCRIPTION OF THE INVENTION

In accordance with the present invention, there are provided novel benzopyran and naphthopyran compounds that may be graphically represented by the following graphic formulae I, II and III, wherein graphic formula I represents the 2-H-benzopyran series and graphic formulae II and III represent the isomeric naphthopyran series.

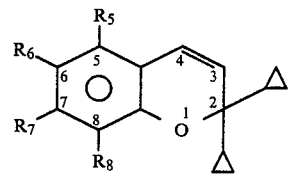

I

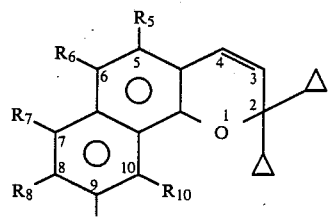

II

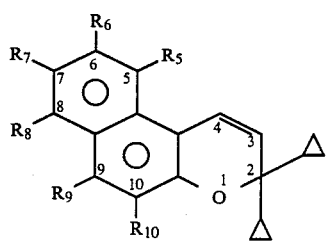

III

A variety of substituents may be placed on the benzo and naphtho portions of the benzopyran and naphthopyran rings. For example, such rings may be substituted in the positions represented respectively by $R_5$–$R_8$ in graphic formula I and $R_5$–$R_{10}$ in graphic formulae II and III with $C_1$–$C_{10}$ straight and branched chain alkyl, $C_5$–$C_7$ cycloalkyl, phenyl, mono- or disubstituted phenyl, $C_1$–$C_4$ alkoxy, halogen, and five or six-membered heterocyclic groups connected to the benzopyran or naphthopyran rings by a single bond. More particularly, the benzo and naphtho portions of the benzopyran or naphthopyran rings may be substituted with $C_1$–$C_5$ alkyl, e.g., methyl, ethyl, n-propyl, isopropyl, butyl, and pentyl, $C_5$–$C_6$ cycloalkyl, e.g., cyclopentyl and cyclohexyl, $C_1$–$C_3$ alkoxy, e.g., methoxy, ethoxy and propoxy, chlorine (chloro), bromine (bromo), furyl, thienyl, phenyl, and ortho-, meta- or para-substituted phenyl, wherein the phenyl substituent is selected from the group consisting of $C_1$–$C_4$ alkyl, $C_1$–$C_4$ alkoxy, chloro and bromo. Preferably, the phenyl group is substituted with one substituent and that substituent is in the para position, e.g., p-methyl phenyl, p-chloro phenyl and p-methoxy phenyl. Still more particularly, the benzo or naphtho portion of the benzopyran or naphthopyran rings may be substituted with $C_1$–$C_3$ alkyl, $C_1$–$C_3$ alkoxy, e.g., methoxy, ethoxy and propoxy, chlorine (chloro), bromine (bromo), phenyl, and $C_1$–$C_3$ alkoxy phenyl, e.g., p-methoxy phenyl. When the benzopyran and naphthopyran rings are not substituted at positions represented by $R_5$–$R_{10}$ with one of the aforementioned substituent groups, $R_5$–$R_{10}$ are hydrogen.

In naming and referring to the benzopyran and naphthopyran compounds of graphic formulae I–III, positions on the rings are numbered counterclockwise starting with the oxygen atom as number (1). Such positions are indicated by the numbers appearing on the inside of the rings depicted in graphic formulae I–III. As shown in graphic formula I, the benzopyran ring may be substituted at the 5, 6, 7 and/or 8 positions, i.e., $R_5$, $R_6$, $R_7$ and/or $R_8$. In certain embodiments, the benzo portion of the benzopyran ring is substituted at the 5- position or the 5- and 8-positions, i.e., $R_5$ or $R_5$ and $R_8$. In such respective embodiments, $R_6$–$R_8$ or $R_6$ and $R_7$ are each hydrogen.

As shown in graphic formulae II and III, the naphtho portion of the naphthopyran ring may be substituted at the 5, 6, 7, 8, 9 and/or 10 position, i.e., $R_5$–$R_{10}$. In certain embodiments, the naphtho portion of the naphthopyran ring is substituted at the 5- position, at the 5- and 6-positions or the 5- and 9-positions, i.e , $R_5$, $R_5$ and $R_6$, or $R_5$ and $R_9$. In such embodiments, $R_6$–$R_{10}$, $R_7$–$R_{10}$ or $R_6$–$R_8$ are respectively each hydrogen.

Of particular current interest are the following benzopyrans and naphthopyrans:

(1) 2,2-dicyclopropyl[2-H-1,2b]benzopyran
(2) 5-methyl-2,2-dicyclopropyl[2-H-1,2b]benzopyran
(3) 7-methoxy-2,2-dicyclopropyl[2-H-1,2b]benzopyran
(4) 2,2-dicyclopropyl[2-H-1,2b]naphthopyran
(5) 5-methyl-2,2-dicyclopropyl[2-H-1,2b]naphthopyran
(6) 5-isopropyl-2,2-dicyclopropyl[2-H-1,2b]naphthopyran
(7) 9-methoxy-2,2-dicyclopropyl[2-H-1,2b]naphthopyran
(8) 6-p-methoxyphenyl-9-methoxy-2,2-dicyclopropyl[2-H-1,2b]naphthopyran
(9) 6-p-methoxyphenyl-5-methyl-2,2-dicyclopropyl[2-H-1,2b]naphthopyran
(10) 6-chloro-2,2-dicyclopropyl[2-H-1,2b]naphthopyran
(11) 5-methyl-6-chloro-2,2-dicyclopropyl[2-H-1,2b]naphthopyran
(12) 5-methyl-9-methoxy-2,2-dicyclopropy[2-H-1,2b]naphthopyran
(13) 5-methyl-7-methoxy-2,2-dicyclopropyl[2-H-1,2b]naphthopyran
(14) 5-methyl-6-chloro-9-methoxy-2,2-dicyclopropyl[2-H-1,2b]naphthopyran Introduction of the two cyclopropyl groups at the 2-position of the naphthopyran ring causes a deeper color and a bathochromic shift in the visible spectra of their corresponding activated forms compared to 2-dialkyl substituted naphthopyrans, and tends to cause an increase in the quantum yield for coloring in the ultraviolet light region, while providing a fast thermal fade at ambient temperatures, vis-a-vis, 2-dialkyl substituted naphthopyrans. Such properties make compounds of graphic formulae II–III useful in photochromic applications such as lenses for sun glasses, ski goggles, visors, camera lenses, windows, windshields, aircraft transparencies, plastic films and sheets, textiles and coating compositions containing organic photochromic compounds, such as paints. In general, the benzopyrans represented by graphic formula I exhibit color changes from colorless to varying from orange-red to purple in unfiltered sunlight. The naphthopyrans represented by graphic formulae II and III generally exhibit color changes from colorless to from yellow to red-orange.

The benzopyrans and naphthopyrans described herein may be dissolved in common organic solvents such as benzene, toluene, chloroform, ethyl acetate, methyl ethyl ketone, acetone, ethyl alcohol, methyl alcohol, acetonitrile, tetrahydrofuran, dioxane, methyl ether of ethylene glycol, dimethylformamide, dimethylsulfoxide, methyl Cellosolve, morpholine and ethylene glycol. They may also be dispersed in liquids containing water and/or alcohols.

The aforedescribed pyran compounds may also be dissolved in colorless or transparent solutions prepared from transparent organic host materials, e.g., transparent polymers (or copolymers) or blends of such transparent polymers and optionally a suitable organic solvent, e.g., polymers of transparent organic host materials described hereinafter dissolved in one or more of the aforesaid described organic solvents. Examples of such solutions include a poly(vinyl acetate)-acetone solution, a nitrocellulose-acetonitrile solution, a poly(vinyl chloride)-methyl ethyl ketone solution, a poly(methylmethacrylate)acetone solution, a cellulose acetate-dimethylformamide solution, a poly(vinyl pyrrolidone)-acetonitrile solution, a polystyrene-benzene solution and an ethyl cellulose-methylene chloride solution. The aforesaid photochromic solutions or compositions may be applied to a compatible host material, e.g., a transparent support, such as cellulose triacetate, polyethylene terephthalate or baryta paper and dried to obtain an article that will develop color on exposure to ultraviolet radiation and that will return to a colorless state by removing the source of ultraviolet radiation.

The pyran compounds described herein (or compositions containing them) may be applied to or incorporated within a coating composition applied to a compatible support; or applied to or incorporated within the article comprising the compatible host, e.g., a polymerized organic material such as a synthetic polymeric plastic host material.

The benzopyrans and naphthopyrans described hereinabove are soluble in the synthetic plastic materials customarily used for plastic lenses, both plano and ophthalmic, e.g., materials such as methyl methacrylate, polycarbonates and polymerizates prepared from CR®-39 diallyl glycol carbonate monomer. See, for example, U.S. Pat. No. 2,542,386. Of the pyran compounds depicted in graphic formulae I–III, compounds represented by general formula II are currently preferred for lenses for the reason that such compounds exhibit photochromic properties to a marked degree. The term photochromic is used herein to describe the following stated desirable properties for photoreactive lenses; namely (a) a high quantum yield for coloring in the near ultraviolet; (b) a low quantum yield for bleaching with visible light; and (c) a fast thermal fade at ambient temperatures, but not so fast that the photochromic material does not color in unfiltered sunlight at ambient temperatures. In addition, the aforesaid properties are desirably retained in conventional rigid synthetic plastic materials customarily used for ophthalmic and plano lenses when such materials are treated to contain such pyran compounds.

On irradiation of the compounds of formula II with ultraviolet light, the naphthopyran ring opens reversibly at the carbon-oxygen bond between the 2-carbon and ring oxygen to form cis and trans structures. The formation of the open form of the compound is believed to be responsible for the coloring of the compounds on exposure to ultraviolet light.

The photochromic compounds of graphic formulae I–III, particularly those of formulae II and III, will fade to the colorless state at normal ambient temperatures when not exposed to ultraviolet light. Generally, the cisoid form of the open or colored form of the photochromic compounds will fade more rapidly than the transoid form. The fade rate of the naphthopyran compounds of graphic formula II may be modified, for example, by introducing various substituent groups in the $R_5$ position of the molecule. Generally, the presence of bulky groups in this position will increase the fade rate.

For sunglass applications, 2,2-dicyclopropyl[2H1,2b-naphthopyran] having a $C_1$–$C_5$ alkyl, e.g., methyl, in the 5-position ($R_5$) and its derivatives, i.e., compounds substituted additionally on the naphthalene ring, e.g., at the 6- or 9-position are currently preferred. Examples of specific derivatives are those in which $R_6$ or $R_9$ in graphic formula II represents $C_1$–$C_4$ alkyl, (e.g., methyl), chlorine, bromine, $C_1$–$C_4$ alkoxy, e.g., methoxy, phenyl, or $C_1$–$C_4$ alkoxy phenyl, e.g. methoxyphenyl. It is expected that benzopyrans of graphic formula I with alkoxy substituents in the benzo group will exhibit an orange-reddish color in the open form while the naphthopyrans of graphic formulae II and III will exhibit a yellow-orange to red-orange color in the open form when irradiated. For example, 5-methyl-9-methoxy-2,2-dicyclopropyl[2H1,2b-naphthopyran] has an orange-red colored form.

The compounds of the present invention may be prepared by a process based on a Claisen rearrangement. In such process, the benzopyran and naphthopyran compounds described herein are prepared by heating the appropriate phenol or naphthol with 1,1-dicyclopropylpropynol in an organic solvent and in the presence of a suitable acid catalyst under mild reaction conditions for a time sufficient to complete the reaction, i.e., usually between about 2 and about 6 hours. Organic solvents that may be used include xylene and toluene. Reaction temperatures will vary and typically range from about 100° C. to about 160° C. The particular reaction temperature will be a function of the boiling point of the chosen solvent. For example, when xylene is used as the solvent, reaction temperatures will generally be about 140° C., whereas if toluene is used as the solvent, reaction temperatures will typically be about 110° C. Examples of suitable acid catalysts include sulfuric acid, polyphosphoric acid, acidic alumina or other acid catalysts. The reaction for the benzopyran of graphic formula I may be expressed by the following equation:

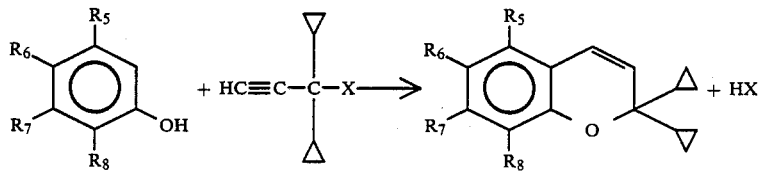

wherein $R_5$, $R_6$, $R_7$ and $R_8$ are the same as defined with respect to graphic formula I and X is hydroxyl, chloro, or acetoxy [$CH_3C(O)O-$]. In place of the phenol depicted in the above equation, a corresponding naphthol may be used to prepare naphthopyrans of graphic formulae II and III. The 1,1-dicyclopropyl-1-propynol reactant may be prepared by reacting dicyclopropyl ketone, which is commercially available, with lithium acetylide, which is commercially available as an ethylene diamine complex, in a suitable organic solvent, such as tetrahydrofuran, dimethyl sulfoxide or toluene, followed by acidification with mineral acid. The 1,1-dicyclopropyl-1-propynol reactant is obtained in near quantitative yields.

Conventional photoreactive inorganic glass lenses containing silver halide particles darken to a gray or brown color in sunlight. In order to duplicate this color change in a plastic lens using the organic photochromic chromenes described in this application, such compounds may be mixed or used in conjunction with other appropriate organic Photochromic materials to produce the desired gray or brown color shade on exposure to ultraviolet light. For example, a compound which colors to yellow can be blended with a compound that colors to an appropriate purple to produce a brown shade. Similarly, a compound which is orange in its colored state will produce a shade of gray in conjunction with an appropriate blue coloring compound.

Many of the spiro(indolino) pyrido benzoxazine photochromic compounds described in U.S. Pat. No. 4,637,698 and spiro(indolino) naphthoxazines described in U.S. Pat. Nos. 3,562,172, 3,578,602, 4,215,010 and 4,342,668 color to purple or blue when activated, and these compounds may be used in admixture with or in conjunction with the yellow or orange/red photochromic compounds described in this application to obtain a near gray or brown color when exposed to unfiltered sunlight.

Such spiro(indolino)-type compounds may be represented by the following graphic formula:

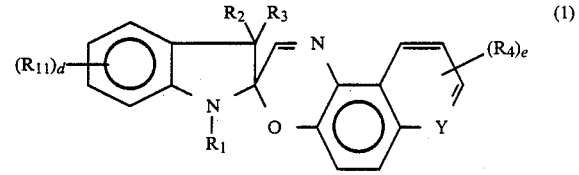

In the above graphic formula (1), $R_1$ is selected from the group consisting of $C_1$–$C_8$ alkyl, e.g., methyl, ethyl, propyl, butyl, etc., phenyl, phen($C_1$–$C_4$)alkyl, e.g., benzyl, naphth($C_1$–$C_4$)alkyl, e.g., 1-naphthylmethyl, allyl, acrylyl($C_2$–$C_6$)alkyl, methacrylyl($C_2$–$C_6$)alkyl, carboxy($C_2$–$C_6$)alkyl, e.g., β-carboxyethyl, γ-carboxypropyl, δ-carboxybutyl, cyano ($C_2$–$C_6$)alkyl, e.g., β-cyanoethyl, γ-cyanopropyl, β- cyanoisopropyl, and δ-cyanobutyl, $C_1$–$C_4$ acyloxy($C_2$–$C_6$)alkyl, i.e., [$R_cC(O)OR_d$-, wherein $R_c$ is a $C_1$–$C_4$ alkyl and $R_d$ is a $C_2$–$C_6$ alkyl], e.g., acetoxyethyl, acetoxypropyl, propionyloxyethyl, acetoxybutyl, and propionyloxypropyl, hydroxy($C_2$–$C_6$)alkyl, e.g., hydroxyethyl, hydroxypropyl and hydroxybutyl, ($C_2H_4O$)$_m$.$CH_3$, wherein m is an integer of from 1 to 6, and mono- and disubstituted phenyl, said phenyl substituents being selected from $C_1-C_4$ alkyl and $C_1-C_5$ alkoxy, e.g., methoxy ethoxy, propoxy, butoxy and pentoxy. Preferably, $R_1$ is selected from the group consisting of $C_1-C_4$ alkyl, phenyl, benzyl, 1-naphth($C_1-C_2$)alkyl, such as 1-naphthylmethyl, carboxy($C_2-C_4$)alkyl, cyano($C_2-C_4$)alkyl, $C_1-C_4$ acyloxy($C_2-C_4$)alkyl, e.g., $C_1-C_4$ acyloxyethyl, hydroxy($C_2-C_4$)alkyl, e.g., $(C_2H_4O)_m.CH_3$, wherein m is an integer of from 1 to 3, e.g., 2.

$R_2$ and $R_3$ of the above graphic formula (1) are each selected from the group consisting of $C_1-C_5$ alkyl, phenyl, mono- and disubstituted phenyl, benzyl, or $R_2$ and $R_3$ may combine to form a cyclic ring selected from the group consisting of an alicyclic ring containing from 6 to 8 carbon atoms (including the spiro carbon atom), norbornyl and adamantyl. The aforesaid phenyl substituents may be selected from $C_1-C_4$ alkyl and $C_1-C_5$ alkoxy radicals. More particularly, $R_2$ and $R_3$ are each selected from $C_1-C_5$ alkyl, e.g., methyl, ethyl, propyl, butyl and pentyl, and phenyl. When one of $R_2$ or $R_3$ is a tertiary alkyl radical, such as tertiary butyl or tertiary amyl, the other is preferably an alkyl radical other than a tertiary alkyl radical.

Y in the graphic formula (1) may be carbon or nitrogen. The number and type of non-hydrogen substituent groups represented by $R_4$ will vary depending upon whether Y is carbon or nitrogen. Generally, when Y is carbon each $R_4$ substituent may be selected from the group consisting of halogen, e.g., chloro, fluoro, or bromo, $C_1-C_5$ alkyl, $C_1-C_5$ alkoxy, e.g., methoxy, ethoxy, propoxy, butoxy and pentoxy, nitro, cyano, thiocyano, $C_1-C_4$ monohaloalkyl, e.g., $C_1-C_4$ monochloroalkyl, such as chloromethyl and chloroethyl, $C_1-C_2$ polyhaloalkyl, as, for example, trihaloalkyl such as trichloroalkyl or trifluoroalkyl, e.g., trifluoromethyl and 2,2,2-trifluoroethyl, and monoalkylamino or dialkylamino wherein the alkyl moiety of the alkylamino group contains between one to four carbon atoms, e.g., methylamino, ethylamino, propylamino, dimethylamino and diethylamino.

The letter "e" in the graphic formula (1) is a number of from 0 to 1 or 2, e.g., 1, and denotes the number of non-hydrogen substituents. In particular, when "e" is 1 or 2 and Y is carbon, each $R_4$ substituent may be selected from the group $C_1-C_2$ alkyl, $C_1-C_2$ alkoxy, chloro, fluoro, bromo, nitro, and trifluormethyl. When "e" is 0 (zero), there are no non-hydrogen substituents and all of the aromatic carbon atoms have their full complement of hydrogen atoms.

When Y is nitrogen, each $R_4$ non-hydrogen substituent may be selected from $C_1-C_5$ alkyl, e.g., $C_1-C_2$ alkyl, $C_1-C_5$ alkoxy, e.g., $C_1-C_2$ alkoxy, and halogen, e.g., chloro, fluoro or bromo. Typically, "e" is 0 (zero) when Y is nitrogen and thus there are no non-hydrogen substituents.

$R_{11}$ in the graphic formula (1) may be selected from $C_1-C_5$ alkyl, halogen, $C_1-C_5$ alkoxy, nitro, cyano, $C_1-C_4$ monohaloalkyl, $C_1-C_4$ polyhaloalkyl, $C_1-C_8$ alkoxycarbonyl, $C_1-C_4$ acyloxy, i.e., $R_cC(O)O-$, wherein $R_c$ is a $C_1-C_4$ alkyl, e.g., methyl. The letter "d" in graphic formula (1) may vary from 0 to 4, e.g., 0 to 2, such as 1 or 2, and denotes the number of non-hydrogen substituents. When "d" is 0 (zero), there are no non-hydrogen substituents as described with respect to "e".

More particularly, the spiro(indolino) pyridobenzoxazines may be represented by the following graphic formula:

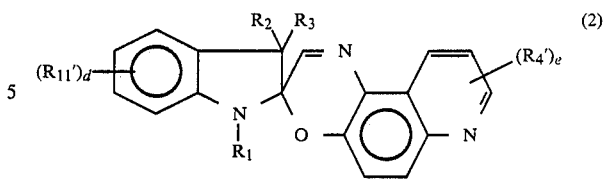

In graphic formula (2), $R_1$, $R_2$ and $R_3$ are the same as defined with respect to graphic formula I. $R_4$ may be selected from $C_1-C_5$ alkyl, e.g., $C_1-C_2$ alkyl, $C_1-C_5$ alkoxy, e.g., $C_1-C_2$ alkoxy and halogen, e.g., chloro, fluoro or bromo. The letter "e" may vary from 0 to 1. Commonly, "e" is 0, and thus, there are no non-hydrogen substituents. When "e" is 1, the $R'_4$ substituent may be located on any one of the available carbon atoms of the pyridobenz moiety of the pyridobenzoxazine portion of the compound, i.e., at the 5', 6', 8', 9' or 10' positions, must usually at the 8', 9' or 10' positions. When "e" is 2, the $R'_4$ substituent may be the same or different and, in either case, are selected from the above-described group and are located at two of the aforedescribed available carbon atoms.

$R'_{11}$ in graphic formula (2) may be selected from the group consisting of $C_1-C_5$ alkyl, e.g., methyl, ethyl, propyl, butyl and pentyl, halogen, e.g., chloro and fluoro, $C_1-C_5$ alkoxy, e.g., methoxy, ethoxy, propoxy, butoxy and pentoxy, nitro, cyano, $C_1-C_4$ monohaloalkyl, e.g., chloromethyl, fluoromethyl, chloroethyl, chloropropyl, etc., $C_1-C_4$ polyhaloalkyl, e.g., trihaloalkyl, $C_1-C_8$ alkoxycarbonyl, and $C_1-C_4$ acyloxy, i.e., $R_cC(O)O-$, wherein $R_c$ is a $C_1-C_4$ alkyl, e.g., methyl. An example of an acyloxy group is acetoxy. While any halogen, i.e., chlorine, bromine, iodine and fluorine may be used in respect to the aforesaid halogen or haloalkyl substituents, chlorine, fluorine and bromine, particularly chlorine and fluorine are preferred for the halogen substituent and fluorine is preferred for the polyhaloalkyl substituent, e.g., trifluoromethyl, ($CF_3$). Preferably, $R'_{11}$ is selected from the group consisting of $C_1-C_2$ alkyl, chlorine, fluorine, $C_1-C_2$ trihaloalkyl, e.g., trihalomethyl such as trifluoromethyl and $C_1-C_5$ alkoxy.

The letter "d" in graphic formula (2) is a number from 0 to 4, e.g., 0 to 2, such as 1 or 2. When "d" is 2 or more, the $R'_{11}$ substituent may be the same or different and in either case, are selected from the aforedescribed group. The $R'_{11}$ substituent(s) may be located on any of the available carbon atoms of the indolino portion of the compound, i.e., at the 4, 5, 6 or 7 positions. When "d" is 2, the $R'_{11}$ substituents may be present at the 4 and 5, 5 and 6, 4 and 7 or 6 and 7 carbon atoms of the indolino moiety.

It is possible that the photochromic organic substances of graphic formula (2) (and 3) can be a mixture of isomers due to the alternative directional mechanism by which intramolecular condensation occurs during formation of the starting indole reactant (Fischer's base). Indolization of 3-substituted phenylhydrazones can give rise to a 4-substituted indole, a 6-substituted indole, or mixtures thereof. Thus, when "d" is 1, the photochromic substance may be substituted at the 4 position on the indoline ring, at the 6 position of that ring or comprise a mixture of such isomers. When "d" is 2, the photochromic substance may be substituted at any combination of the 4, 5, 6, or 7 carbon atoms of the indoline ring (as heretofore indicated) and may comprise an isomeric mixture of such compounds, e.g., a mixture of compounds having substituents at the 4 and 5, 4 and 6, 5 and 6, 4 and 7, 5 and 7, and 6 7 positions of the indoline ring. Commonly, when "d" is 2 the substituents are located at the 4 and 5, or 5 and 6 positions. Also contemplated are materials containing mixtures of such isomers, e.g., materials comprising 4 (and 6) and 5-substituted spiro(indolino benzoxazines.

Examples of spiro(indolino) pyridobenzoxazines selected from the description of graphic formula (2) that may be employed in the process of the present invention are described in Table 1. Such pyridobenzoxazines are those in which $R_1$, $R_2$, $R_3$, and $R'_{11}$ are as indicated in Table 1, the letter "e" is 0 (zero), and the letter "d" is 0, 1 or 2. A hyphen (-) indicates the absence of a non-hydrogen substituent.

TABLE 1

| Compound/ | $R_1$ | $R_2$ | $R_3$ | $R_{11}'$ | $R_{11}'$ |
|---|---|---|---|---|---|
| 1 | $CH_3$ | $CH_3$ | $CH_3$ | — | — |
| 2 | $CH_3$ | $CH_3$ | $CH_3$ | 4-$CH_3$ | 5-$CH_3$ |
| 3 | $CH_3$ | $CH_3$ | $CH_3$ | 5-$OCH_3$ | — |
| 4 | $CH_3$ | $CH_3$ | $CH_3$ | 5-Cl | 6-$CH_3$ |
| 5 | $CH_3$ | $CH_3$ | $C_2H_5$ | — | — |
| 6 | $CH_3$ | $CH_3$ | $C_2H_5$ | 5-$CH_3$ | 6-$CH_3$ |
| 7 | $CH_3$ | $C_2H_5$ | $C_2H_5$ | — | — |
| 8 | n-$C_4H_9$ | $CH_3$ | $C_2H_5$ | — | — |
| 9 | $CH_3$ | $CH_3$ | phenyl | — | — |
| 10 | $CH_3$ | phenyl | phenyl | — | — |
| 11 | $C_2H_5$ | $CH_3$ | $C_2H_5$ | 4-$CH_3$ | 5-$CH_3$ |
| 12 | n-$C_4H_9$ | $CH_3$ | $C_2H_5$ | 5-$CH_3$ | 6-$CH_3$ |
| 13 | $CH_3$ | $CH_3$ | $CH_3$ | 5-$CH_3$ | 6-$CH_3$ |
| 14 | n-$C_3H_7$ | $CH_3$ | $CH_3$ | 5-$OCH_3$ | — |

Compound 2 in Table 1 may be named 1,3,3,4,5-pentamethylspiro[indolino-2,3' [3$\underline{H}$] pyrido [3,2-f] [1,4] benzoxazine]. Similarly, compound 6 in Table 1 may be named 1,3,5,6-tetramethyl-3-ethylspiro[indolino-2,3' [3$\underline{H}$] pyrido [3,2-f] [1,4] benzoxazine]. Other compounds in Table 1 can be similarly named taking into account the different substituents. Moreover, compounds selected from the description of graphic formula (2) may be similarly named by substituting the substituents described with respect to $R_1$, $R_2$, $R_3$, $R_4$ and $R'_{11}$ for those found in Table 1. When the letter "e" is 1 or more, the $R'_4$ substituent(s) are given a prime (') designation. Numbering of the pyrido benzoxazine portion of the molecule is counter clockwise starting with the nitrogen atoms of the oxazine ring as the 1' position.

Spiro(indolino)naphthoxazines that may be used in the practice of the present process may be represented by the following graphic formula:

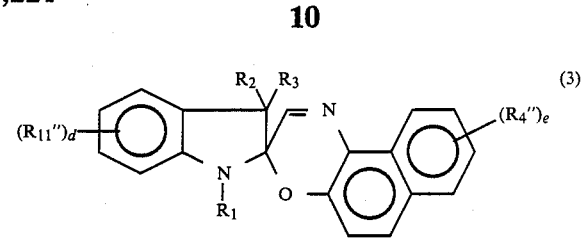

wherein $R_1$, $R_2$ and $R_3$ are the same as that described with respect to graphic formula I.

$R''_4$ in graphic formula (3) may be selected from the group consisting of halogen, e.g., chloro, fluoro, or bromo, $C_1$-$C_5$ alkyl, $C_1$-$C_5$ alkoxy (e.g., methoxy, ethoxy, propoxy, butoxy and pentoxy), nitro, cyano, thiocyano, $C_1$-$C_4$ monohaloalkyl, e.g., $C_1$-$C_4$ monochloroalkyl, such as chloromethyl and chloroethyl, $C_1$-$C_2$ polyhaloalkyl, as for example, trihaloalkyl, such as trichloroalkyl or trifluoroalkyl, e.g., trifluoromethyl and 2,2,2-trifluoroethyl, and monoalkylamino or dialkylamino, wherein the alkyl moiety of the alkylamino group contains from 1 to 4 carbon atoms, e.g., methylamino, ethylamino, propylamino, dimethylamino and diethylamino. More particularly, the $R''_4$ substituent may be selected from the group $C_1$-$C_2$ alkyl, $C_1$-$C_2$ alkoxy, chloro, fluoro, bromo, nitro and trifluormethyl, The letter "e" in graphic formula (3) is a number from 0 to 2, e.g., 1 or 2, and denotes the number of non-hydrogen substituents. When "e" is 0, all of the substituents on the available carbon atoms of the naphtho moiety of the molecule represented by formula (3) are hydrogen.

As in the case with graphic formula (2), when "e" is 1, the $R''_4$ substituent may be located on any of the available carbon atoms of the naphtho moiety of the naphthoxazine portion of the molecule, i.e., at the 5', 6', 7' 8', 9' or 10' positions. Preferably, the $R''_4$ substituent is present on the 7', 8' or 9' carbon atoms. When "e" is 2, the $R''_4$ substituents may be same or different and in either case are selected from the above-described group. When "e" is 2, the $R''_4$ substituents are commonly located at the 7' and 9', or 8' and 10' positions. Numbering of the naphthoxazine portion of the molecule is done in the same manner as that described with regard to the pyrido benzoxazine portion of the molecule of formula (2). $R''_{11}$ and the letter "d" in graphic formula (3) are the same as that described with respect to graphic formula (1).

Non-limiting examples of spiro(indolino) naphthoxazines selected from the description of graphic formula (3) that may be used in the practice of the present invention are described in Table 2. Such spiro(indolino) naphthoxazines are those in which $R_1$, $R_2$, $R_3$, $R''_4$ and $R''_{11}$ are as indicated in Table 2, the letter "d" is 0, 1 or 2 and the letter "e" is 1. As in Table 1, a hyphen (-) indicates the absence of a non-hydrogen substituent. In Table 2, all of the $R''_4$ substituents are at the 9'-position.

TABLE 2

| Compound/ | $R_1$ | $R_2$ | $R_3$ | $R_4$ (9'-) | $R_{11}''$ | $R_{11}''$ |
|---|---|---|---|---|---|---|
| 1 | $CH_3$ | $CH_3$ | $CH_3$ | $OCH_3$ | — | — |
| 2 | $CH_3$ | $CH_3$ | $CH_3$ | $OCH_3$ | 4-$CH_3$ | 6-$CH_3$ |
| 3 | $CH_3$ | $CH_3$ | $CH_3$ | $OCH_3$ | 5-$OCH_3$ | — |
| 4 | $CH_3$ | $CH_3$ | $CH_3$ | $OCH_3$ | 5-Cl | 6-$CH_3$ |
| 5 | $CH_3$ | $CH_3$ | $C_2H_5$ | $OCH_3$ | — | — |
| 6 | $CH_3$ | $CH_3$ | $C_2H_5$ | $OCH_3$ | 5-$CH_3$ | 6-$CH_3$ |
| 7 | $CH_3$ | $C_2H_5$ | $C_2H_5$ | $OCH_3$ | — | — |

TABLE 2-continued

| Compound/ | $R_1$ | $R_2$ | $R_3$ | $R_4$ (9'-) | $R_{11}''$ | $R_{11}''$ |
|---|---|---|---|---|---|---|
| 8 | n-C$_4$H$_9$ | CH$_3$ | C$_2$H$_5$ | OCH$_3$ | — | — |
| 9 | CH$_3$ | CH$_3$ | phenyl | OCH$_3$ | — | — |
| 10 | CH$_3$ | phenyl | phenyl | OCH$_3$ | — | — |
| 11 | CH$_3$ | P-C$_6$H$_4$OCH$_3$ | P-C$_6$H$_4$OCH$_3$ | OCH$_3$ | — | — |
| 12 | C$_2$H$_5$ | CH$_3$ | C$_2$H$_5$ | OCH$_3$ | 5-CH$_3$ | — |
| 13 | n-C$_4$H$_9$ | CH$_3$ | C$_2$H$_5$ | OCH$_3$ | 5-CH$_3$ | — |

Compound 2 in Table 2 may be named 1,3,3,5,6-pentamethyl-9'methoxy-spiro [indolino-2,3' [3H]-naphth [2,1-b] [1,4]-oxazine]. Similarly, compound 6 in Table 2 may be named 1,3,5,6-tetramethyl-3-ethyl-9'-methoxyspiro [indolino-2,3' [3H]-naphth [2,1-b] [1,4]-oxazine. Other compounds in Table 2 can be similarly named taking into account the different substituents. Moreover, compounds selected from the description of graphic formula 3 may be similarly named.

The benzopyran or naphthopyran compounds may be combined with the spiro(indolino) pyrido benzoxazine or spiro(indolino) naphthoxazine compounds in amounts and in a ratio such that the organic host material containing the mixture of compounds exhibits a substantially neutral color when activated with unfiltered sunlight, i.e., as near a neutral color as possible given the colors of the activated pyran and oxazine photochromic compounds. The relative amounts of the oxazine and pyran compounds used will vary and depend in part upon the relative intensities of the color of the activated species of such compounds. Generally, the mole ratio of the spiro (indolino) oxazine compound to the pyran compound will vary from about 1:3 to about 3:1, e.g., between about 1:2 and about 2:1.

Photochromic compounds of the present invention, mixtures of such compounds with other photochromic compounds, or compositions containing same (hereinafter "photochromic substances") may be applied to or incorporated into a host material by various methods. Such methods include dissolving or dispersing the substance within the host material, e.g., imbibition of the photochromic substance into the host material by immersion or thermal transfer; incorporation of the photochromic substance as a separate layer between adjacent layers of the host material; and applying the photochromic substance as a coating to the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms. For example:

(a) The photochromic substance may be mixed with a polymerizable composition that, upon curing, produces a polymeric host material and the polymerizable composition cast as a film, sheet or lens, injection molded or otherwise formed into a sheet or lens, or polymerized by emulsion or suspension polymerization to form a photochromic particulate material that may be used as a pigment;

(b) The photochromic substance may be dissolved or dispersed in water, alcohol or other solvents or solvent mixtures and then imbibed into the solid host material by immersion of the solid host material for from several minutes to several hours, e.g., 2–3 minutes to 2–4 hours, in a bath of such solution or dispersion. The bath is conventionally at an elevated temperature, usually in the range of 50°–120° C.; however, higher temperatures may be used. Thereafter, the host material is removed from the bath and dried;

(c) The photochromic substance may also be applied to the surface of the host material by any convenient manner, such as spraying, brushing, spin-coating or dip-coating from a solution or dispersion of the photochromic substance in the presence of a polymeric binder. Thereafter, the photochromic substance is imbibed into the host material by heating it, e.g., in an oven, for from a minute to several hours, e.g., 2 to 3 hours, at temperatures in the range of from 80°–180° C., e.g., 100°–150° C.;

(d) In a variation of the preceding imbibition procedure, the photochromic substance may be deposited onto or absorbed by a temporary support, e.g., a sheet of kraft paper, aluminum foil, polymer film or fabric, which is then placed in near proximity to or in contact with the host material and heated, e.g., in an oven. This and the preceding procedure may be repeated one or more times to imbibe the desired amount of photochromic substance into the host material;

(e) The photochromic substance may be dissolved or dispersed in a transparent polymeric material which may be applied to the surface of the host in the form of an adherent film by any suitable technique such as spraying, brushing, spin-coating or dip-coating; and finally (f) The photochromic substance may be incorporated in or applied to a transparent polymeric material by any of the above-mentioned methods, which can then be placed within the host material as a discrete layer intermediate to adjacent layers of the host material(s).

In addition, imbibition of photochromic substances into a host material may be accomplished by the method described in U.K. Patent Application No. 2,174,711, which is hereby incorporated in toto by reference. In that method a substantially mottle-free, substantially homogeneous film of polymeric resin having the photochromic substance dissolved therein is applied to the surface of the host material. The film-bearing host material is heated to temperatures near to but below the melting temperature of the photochromic substance for a time sufficient to incorporate a photochromic amount of the photochromic substance into the surface of the host. The photochromic-depleted film is then removed from the host surface with a suitable solvent.

Imbibition of photochromic substances into a host material, e.g., an ophthalmic lens may suitability be carried out by dissolving the photochromic substance in a suitable solvent, e.g., toluene, and absorbing the resulting solution into a temporary substrate, such as filter paper or other substrates described in subparagraph (d) above. The concentration of the photochromic substance in the solvent may vary and will depend on the solubility of the substance in the solvent used. Suitably, the photochromic substance will be present in the solvent at a concentration of from about 5 to 15, e.g., 10, weight percent. The temporary substrate may be a flexible material that can take the shape of the surface of the host material on which it is placed if such surface is irregular or not flat, such as the curved surface of the lens.

The temporary substrate containing the solution of photochromic substances is dried to remove the solvent and the substrate placed in contact with the surface of the host material. Optionally, a metal cap having the shape of the host material surface is placed on top of the temporary substrate to insure uniform contact of the interface of the substrate and host surface. For example, when the host is a lens, the cap and temporary substrate should be shaped to conform to the shape of the lens, e.g., the convex or concave surface of the lens. This sandwich comprising the metal cap-temporary substrate-host material is then heated for a time sufficient to imbibe a photochromic amount of the photochromic substance(s) into the subsurface of the host material. Heating times may range from about 15 minutes to 180 minutes, usually from 45 to 120 minutes at transfer temperatures, which may range from 125° C. to 155° C.

The aforesaid process may be repeated one or more times, e.g., at least twice, to imbibe the desired amount of photochromic substance into the subsurface of the host material, e.g., into a layer of the surface up to about 50 microns thick. In the case of semi-finished lenses, the imbibition process is performed on the front (convex) surface of the lens to allow finishing (grinding) of the back (concave) surface. Further, the edges of the lens may be ground to remove imperfections before thermally transferring the photochromic substances. If desired, the host material may then be tinted with a color compatible dye e.g., a brown, yellow-brown or gray dye.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances are unactivated.

Typically, tinting is accomplished by immersion of the host material in a heated aqueous dispersion of the selected dye. The degree of tint is controlled by the temperature of the dye bath and the length of time the host material is allowed to remain in the bath. Generally, the dye bath is at temperatures of less than 100° C., e.g., from 70° C. to 90° C., such as 80° C., and the host material remains in the bath for less than five (5) minutes, e.g., between about 0.5 and 3 minutes, e.g., about 2 minutes. The degree of tint is such that the resulting article exhibits from about 70 to 85 percent, e.g., 80–82 percent, light transmission.

Adjuvant materials may also be incorporated into the host material with the photochromic substances prior to or subsequent to their application or incorporation into the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers such as hindered amine light stabilizers and singlet oxygen quenchers, such as a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings or coatings that serve as oxygen barriers, e.g., a polyvinyl alcohol coating. Such coatings are known in the art.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open-form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent material or an optically clear material, e.g., materials suitable for ophthalmic elements, such as ophthalmic lenses, or materials useful for applications such as windows, windshields, aircraft transparencies, etc.

Examples of host materials which may be used with the photochromic substances or compositions described herein include: Polymers, i.e., homopolymers and copolymers, of polyol(allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate) copoly(styrene-acrylonitrile), polyvinylbutyral and polymers, i.e., homocopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of the transparent polymers are also suitable as host materials. Preferably, the host material is an optically clear polymerized organic material prepared from a polycarbonate resin, such as the carbonate-linked resin derived from bisphenol A and phosgene, which is sold under the trademark, LEXAN; a poly(methyl methacrylate), such as the material sold under the trademark, PLEXIGLAS; polymerizates of a polyol(allyl carbonate), especially diethylene glycol bis(allyl carbonate), which monomer is sold under the trademark CR-39, and copolymers of diethylene glycol bis(allyl carbonate) with other copolymerizable monomeric materials, e.g., copolymers with for example vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, cellulose acetate, cellulose propionate, cellulose butyrate, cellulose acetate butyrate, and polystyrene and copolymers of styrene with methyl methacrylate, vinyl acetate and acrylonitrile.

Polyol (allyl carbonate) monomers which may be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g, glycols. The monomers can be prepared by procedures well known in the art, e.g., U.S. Pat. Nos. 2,370,567 and 2,403,113.

The polyol (allyl carbonate) monomers may be represented by the graphic formula:

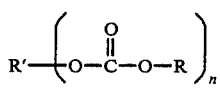 (IV)

wherein R is the radical derived from an unsaturated alcohol and is commonly an allyl or substituted allyl group, R' is the radical derived from the polyol, and n is a whole number from 2–5, preferably 2. The allyl group (R) can be substituted at the 2 position with a halogen, most notably chlorine or bromine, or an alkyl group containing from 1 to 4 carbon atoms, generally a methyl or ethyl group. The R group can be represented by the graphic formula:

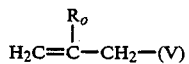

wherein $R_o$ is hydrogen, halogen, or a $C_1$–$C_4$ alkyl group. Specific examples of R include the groups: allyl, 2-chloroallyl, 2-bromoallyl, 2-fluoroallyl, 2-methylallyl, 2-ethylallyl, 2-isopropylallyl, 2-n-propylallyl, and 2-n-butylallyl. Most commonly R is the allyl group, $H_2C=CH-CH_2-$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$–$C_4$) alkylene glycol, i.e., ethylene glycol, propylene glycol, trimethylene glycol, tetramethylene glycol, or diethylene glycol, triethylene glycol, etc.

The aromatic polyol can be represented by the graphic formula:

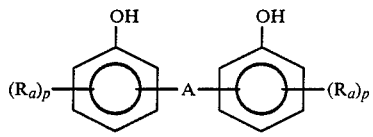 (VI)

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene (isopropylidene), $R_a$ represents lower alkyl substituents of from 1 to 3 carbon atoms and halogen, e.g., chlorine and bromine, and p is 0, 1, 2, or 3. Preferably, the hydroxyl group is in the ortho or para position.

Specific examples of the radical R' include: alkylene groups containing from 2 to 10 carbon atoms such as ethylene, ($-CH_2-CH_2-$), trimethylene, methylethylene, tetramethylene, ethylethylene, pentamethylene, hexamethylene, 2-methylhexamethylene, octamethylene, and decamethylene; alkylene ether groups such as $-CH_2-O-CH_2-$, $-CH_2CH_2-O-CH_2CH_2-$, $-CH_2-O-CH_2-CH_2-$, and $-CH_2CH_2-O-CH_2CH_2CH_2-$; alkylene polyether groups such as $-CH_2CH_2-O-CH_2CH_2-O-CH_2CH_2-$, and $-CH_2CH_2CH_2-O-CH_2CH_2CH_2-O-CH_2CH_2CH_2-$; alkylene carbonate and alkylene ether carbonate groups such as $-CH_2CH_2-O-CO-O-CH_2CH_2-$ and $-CH_2CH_2-O-CH_2CH_2-O-CO-O-CH_2CH_2-O-CH_2CH_2-$; and isopropylidene bis(para-phenyl),

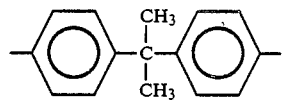

Most commonly, R' is $-CH_2CH_2-$, $-CH_2CH_2-O-CH_2CH_2-$, or $-CH_2CH_2-O-CH_2CH_2-O-CH_2CH_2-$.

Specific non-limiting examples of polyol (allyl carbonate) monomers include ethylene glycol bis(2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

Industrially important polyol bis(allyl carbonate) monomers which may be utilized in the invention herein contemplated are:

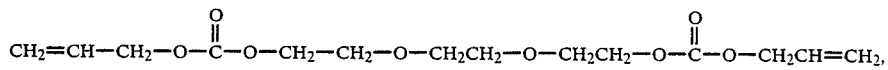

Triethylene Glycol bis(Allyl Carbonate)

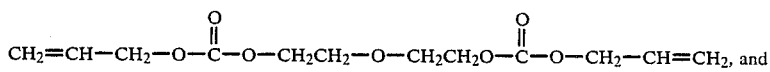 and

Diethylene Glycol bis(Allyl Carbonate)

Ethylene Glycol bis(Allyl Carbonate)

Diethylene glycol bis(allyl carbonate) is preferred.

Because of the process by which the polyol(allyl carbonate) monomer is prepared, i.e., by phosgenation of the polyol (or allyl alcohol) and subsequent esterification by the allyl alcohol (or polyol), the monomer product can contain related monomer species in which the moiety connecting the allyl carbonate groups contains one or more carbonate groups. These related monomer species can be represented by the graphic formula:

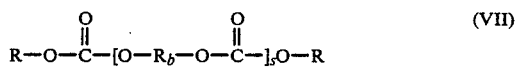 (VII)

wherein R is as defined above, $R_b$ is a bivalent radical, e.g., alkylene or phenylene, derived from a diol, and s is a whole number from 2 to 5. The related monomer species of diethylene glycol bis(allyl carbonate) can be represented by the graphic formula,

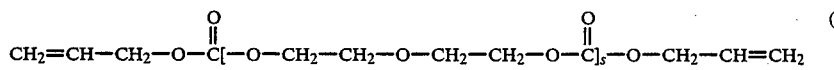 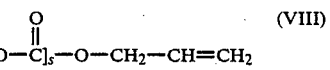 (VIII)

wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4 etc.

In addition, a partially polymerized form of the polyol (allyl carbonate) monomer, i.e., prepolymer, can be used. In that embodiment, the monomer is thickened by heating or partially polymerized by using small, e.g., 0.5–1.5 parts of initiator per hundred parts of monomer (phm), to provide a non-gel containing, more viscous monomeric material.

As used in the present description and claims, the term polyol(allyl carbonate) monomer or like names, e.g., diethylene glycol bis(allyl carbonate), are intended to mean and include the named monomer or prepolymer and any related monomer species contained therein.

Polyfunctional acrylate monomers that may be used to prepare synthetic polymeric host materials are esterification products of an acrylic acid moiety selected from the group consisting of acrylic acid and methacrylic acid, and a polyol, e.g., a diol, a triol or tetracarbinol. More particularly, the polyfunctional acrylate monomer may be represented by the following graphic formula:

$$(CH_2=C(R_t)-C(O))_n R'' \quad (IX)$$

wherein $R_t$ is hydrogen or methyl, n is the number 2, 3 or 4, and R'' is the multivalent radical, i.e., a bivalent, trivalent or quadravalent radical, remaining after removal of the hydroxy groups from a polyol, having from 2 to 4 hydroxy groups, e.g., a diol, a triol or tetracarbinol respectively. More particularly, $R_t$ is hydrogen or methyl, and n is 2 or 3, more usually 2.

R'' may be selected from the group consisting of alpha, omega $C_2$–$C_8$ glycols, cyclohexane diol, diethylene glycol, triethylene glycol, tetraethylene glycol, dipropylene glycol, $C_2$–$C_5$ triols and pentaerythritol. Examples of such polyols include ethylene glycol, trimethylene glycol, 1,4-butane diol, 1,5-pentane diol, 1,6-hexane diol, propylene glycol, trimethylol propane, glycerol and the like.

Examples of polyfunctional acrylate monomers, such as diacrylates and triacrylates, include: ethylene glycol diacrylate, ethylene glycol dimethacrylate, 1,2-propane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-dimethyl-1,6-hexane diol dimethacrylate, diethylene glycol diacrylate, diethylene glycol dimethacrylate, triethylene glycol dimethyacrylate, trimethylol propane trimethacrylate, tetraethylene glycol diacrylate, tetraethylene glycol dimethacrylate, dipropylene glycol diacrylate, dipropylene glycol dimethacrylate, trimethylol propane triacrylate, glycerol triacrylate, glycerol trimethacrylate, pentaerythritol triacrylate, pentaerythritol dimethacrylate, pentaerythritol tetraacrylate, pentaerythritol tetramethacrylate and mixtures of such acrylate monomers.

A portion of the polyfunctional acrylate monomer may be replaced with a monofunctional copolymerizable monomer containing the vinyl ($CH_2=CH-$) grouping. Such compatible monomers include monofunctional acrylic and methacrylic acid esters, and vinyl esters of $C_2$–$C_6$ carboxylic acids, i.e., vinyl carboxylates. Preferably, the copolymerizable monomer is a non-aromatic, e.g., non-benzenoid, containing monomer. Monofunctional acrylic or methacrylic ester monomers may be graphically illustrated by the following formula, $$CH_2=C(R_t)-C(O)-O-R''' \quad (X)$$

wherein $R_t$ is hydrogen or methyl, and R is selected from the group consisting of $C_1$–$C_{12}$, e.g., $C_1$–$C_8$, alkyl, $C_5$–$C_6$ cycloalkyl, glycidyl and hydroxyethyl. Preferably, R''' is a a $C_1$–$C_4$ alkyl, e.g., methyl or cyclohexyl.

Examples of monofunctional acrylic acid type monomers include, for example, the acrylic and methacrylic acid esters of alkanols such as methanol, ethanol, propanol, butanol, pentanol, hexanol, heptanol and octanol, e.g., methyl acrylate, methyl methacrylate, ethyl acrylate and ethyl methacrylate, cycloalkanols such as cyclopentanol and cyclohexanol, glycidol (3-hydroxy propylene oxide, (d, 1, dl)) and ethylene glycol. Examples of vinyl carboxylates include vinyl acetate, vinyl propionate, vinyl butyrate and vinyl valerate. In addition to and/or in place of the aforedescribed monofunctional copolymerizable monomer, monofunctional allylic and difunctional allylic copolymerizable compatible monomers may also replace a portion of the polyfunctional acrylate monomer. Monofunctional allylic monomers contemplated include allyl esters of $C_2$–$C_6$ carboxylic acids, $C_1$–$C_6$ allyl ethers and other copolymerizable allyl compounds. Preferably the monofunctional allylic monomer is a non-aromatic compound. Difunctional allylic copolymerizable monomers contemplated herein are the polyol (allyl carbonates) monomers of graphic formula VI.

The amount of photochromic substance or composition-containing same applied to or incorporated into a host material is not critical provided that a sufficient amount is used to produce a photochromic effect discernible to the naked eye. Generally such amount can be described as a photochromic amount. The amount used depends often upon the intensity of color desired upon irradiation thereof and upon the method used to incorporate or apply the photochromic substances. Typically, the more compound applied or incorporated, the greater is the color intensity. Usually, the amount of each photochromic substance incorporated into or applied to the host material ranges from about 0.01 to about 20 percent by weight, more usually from about 0.05 to about 10 percent by weight, based on the weight of the host material. Stated another way, the amount of each photochromic substance used to impart a photochromic effect will typically vary from about 0.1 to about 10, e.g., 0.5 to 2 milligrams of the photochromic substance per square inch of the surface of the host material independent of the thickness of the host material article.

The present invention is more particularly described in the following examples which are intended as illustrative only, since numerous modifications and variations therein will be apparent to those skilled in the art.

EXAMPLE 1

Lithium acetylide/ethylene diamine complex (10 grams, 0.1 mole) was added in small portions over 30 minutes to a solution of dicyclopropyl ketone (11 grams, 0.1 mole) in 50 cubic centimeters (cc) of dimethyl sulfoxide at room temperature. The reaction mixture was left at room temperature overnight and then poured onto 500 grams of crushed ice. The cooled reaction mixture was acidified with dilute (10 percent) hydrochloric acid and the organic reaction product extracted with diethyl ether (2×100 cc). The ether extract was dried over anhydrous magnesium sulfate, filtered, and the ether solvent distilled from the filtrate leaving as a colorless oil, 1,1-Dicyclopropylpropyn-1-ol in quantitative yield.

EXAMPLE 2

1,1-Dicyclopropylpropyn-1-ol (3.68 grams, 0.0267 moles) and 1-naphthol (4.2 grams, 0.03 moles) were dissolved in toluene (30 cc). One drop of concentrated sulfuric acid was added to the toluene solution, which was boiled under reflux for 3 hours. The reaction solution was cooled and then washed sequentially with dilute (10 percent) sodium hydroxide and water. The organic layer was extracted with diethyl ether (2×50 cc), dried over anhydrous magnesium sulfate and filtered. Ether solvent was distilled off and the residual brown oil was chromatographed on silca gel using a 1:9 mixture of ethyl acetate and petroleum (boiling point 60°–80° C.) as eluant. The photochromic fraction in the eluate was collected and the solvent removed by distillation. On concentration, product crystals of 2,2-Dicyclopropyl-[2-H-1,2b] naphthopyran (i.e., graphic formula II) separated. The product had a melting point of 51° C. The aforesaid naphthopyran exhibits a reversible change from colorless to orange on exposure to a flash from a flash gun from which the plastic cover of the lamp had been removed.

EXAMPLE 3

Acidic alumina (20 grams) was added to a solution of 2-naphthol (4.2 grams, 0.03 moles) and 1,1-Dicyclopropylpropyn-1-ol (3.08 grams, 0.0226 moles) in toluene (30 cc). The mixture was boiled under reflux for three hours and the alumina removed by filtration. The filtrate was washed sequentially with a dilute (10 percent) sodium hydroxide solution and water. The organic layer was extracted with diethyl ether (2×50 cc), dried over anhydrous magnesium sulfate, and filtered. The filtrate was evaporated under reduced pressure leaving a brown oil which was chromatographed on silica gel using petroleum (b.p. 60°–80° C.) as the eluant. The fraction which exhibited a reversible change from colorless to yellow on exposure to the flash from the flash gun of Example 2 was collected. Petroleum solvent was removed under reduced pressure leaving as a colorless oil 0.3 grams of 2,2-Dicyclopropyl- [2-H-2,1b] naphthopyran (i.e., graphic formula III).

EXAMPLE 4

Acidic alumina (60 grams) was added to a solution of 3-methyl-1-naphthol (15.8 grams, 0.1 mole) and 1,1-Dicyclopropylpropyn-1-ol (13.6 grams, 0.1 mole) in toluene (100 cc). The reaction mixture was boiled under reflux for 3 hours and the alumina removed by filtration. The filtrate was washed sequentially with a dilute (10 percent) sodium hydroxide solution and water. The organic layer was extracted with diethyl ether (2×50 cc), dried over anhydrous magnesium sulfate and filtered. The filtrate was evaporated under reduced pressure leaving a brown oil which was chromatographed on silica gel using petroleum (b.p. 60°–80° C.) as the eluant. The fraction which exhibited a reversible change from colorless to orange on exposure to the flash from the flash gun of Example 2 was separated and the solvent removed under reduced pressure leaving as a colorless oil 2 grams of 2,2-Dicyclopropyl-5-methyl-[2-H-1,2b] naphthopyran.

EXAMPLE 5

Following the procedure of Example 4, acidic alumina (15 grams) was added to a solution of 7-methoxy-3-methyl-1naphthol (4.5 grams, 0.027 mole) and 1,1-Dicyclopropylpropyn-1-ol (3.67 grams, 0.027 mole) in toluene (50 cc). The reaction mixture was boiled under reflux for three hours and the alumina removed by filtration. The filtrate was worked-up in the manner described in Example 4. The chromatographed fraction which exhibited a reversible change from colorless to orange-red on exposure to the flash from the flash gun of Example 2 was separated and the solvent removed leaving as a colorless oil 0.2 grams of 2,2-Dicyclopropyl-9-methoxy-5-methyl-[2-H-1,2b] naphthopyran.

EXAMPLE 6

Phenol (9.4 grams, 0.1 mole) was added to a reaction vessel containing 1,1-Dicyclopropyn-1-ol (13.6 grams, 0.1 mole), acidic alumina (60 grams) and toluene (80 milliliters). The reaction mixture was boiled under reflux for 3 hours after which the alumina was removed by filtration. The filtrate was washed with a dilute (10 percent) aqueous sodium hydroxide solution and the organic layer was dried over anhydrous magnesium sulfate and then filtered. The solvent in the organic layer was distilled off under reduced pressure leaving an oil which was chromatographed on silica gel using petroleum (b.p. 60°-80° C.) as the eluant. The fraction which changed from colorless to purple at −70° C. on exposure to light from the flash gun of Example 2 was separated. The solvent in that fraction was distilled off leaving as a colorless oil 4 grams of 2,2-Dicyclopropyl-benzopyran.

EXAMPLE 7

Following the procedure of Example 6, p-Methoxyphenol (6.25 grams, 0.05 mole) was added to a reaction vessel containing 1,1-Dicyclopropyn-1-ol (6.8 grams, 0.05 mole), acidic alumina (30 grams) and toluene (50 milliliters). The reaction mixture was boiled under reflux for 3 hours after which the alumina was removed by filtration. The filtrate was washed with a 10 percent aqueous sodium hydroxide solution and the resulting organic layer dried over anhydrous magnesium sulfate and then filtered. The solvent in the organic layer was removed leaving an oil which was thrice chromatographed on silica gel using petroleum (b.p. 60°-80° C.) as eluant. The fraction which changed from colorless to red-orange at 0° C. on exposure to light from the flash gun of Example 2 was separated. The solvent in that fraction was removed leaving as a colorless oil 0.5 grams of 6-methoxy-2-2-Dicyclopropylbenzopyran.

EXAMPLE 8

Following the procedure of Example 6, m-Methoxyphenol (6.2 grams, 0.05 mole) was added to a reaction vessel containing 1,1-Dicyclopropyn-1-ol (6.8 grams, 0.05 mole), acidic alumina (30 grams) and toluene (50 milliliters). The reaction mixture was boiled under reflux for 3 hours after which the alumina was removed by filtration. The filtrate was washed with a 10 percent aqueous sodium hydroxide solution to remove unreacted m-Methoxyphenol and the resulting organic layer was dried over anhydrous magnesium sulfate. The solvent in the organic layer was removed leaving an oil which from nuclear magnetic resonance (n.m.r.) spectroscopy was a 1:4 mixture of the isomeric 5- and 7-methoxy-2,2-dicyclopropylbenzopyran. The 7-methoxy benzopyran isomer was separated by chromatography on silica gel using petroleum (b.p. 60°-80° C.) as the eluant. This isomer (0.3 grams) changed from colorless to red-orange at room temperature when exposed to light from the flash gun of Example 2 .

Although the present invention has been described with reference to specific details of certain embodiments thereof, it is not intended that such details should be regarded as limitations upon the scope of the invention except as and to the extent that they are included in the accompanying claims.

What is claimed is:
1. A compound represented by one of the following graphic formulae:

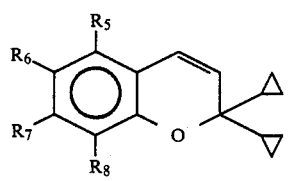

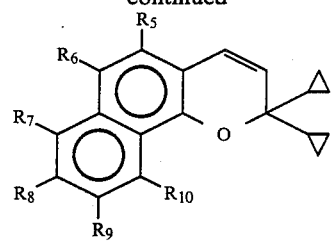

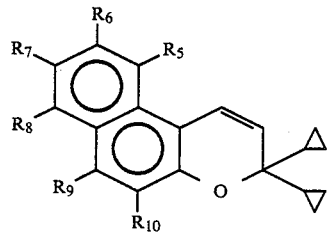

wherein $R_5$–$R_{10}$ are each selected from the group consisting of hydrogen, $C_1$–$C_{10}$ alkyl, $C_5$–$C_7$ cycloalkyl, $C_1$–$C_4$ alkoxy, halogen, furyl, thienyl, phenyl, substituted phenyl, wherein the phenyl substituent is selected from the group consisting of $C_1$–$C_4$ alkyl, $C_1$–$C_4$ alkoxy, chloro and bromo.

2. A compound according to claim 1 wherein $R_5$–$R_{10}$ are each selected from the group consisting of hydrogen, $C_1$–$C_5$ alkyl, $C_5$–$C_6$ cycloalkyl, $C_1$–$C_3$ alkoxy, $C_1$–$C_4$ alkoxyphenyl, $C_1$–$C_4$ alkylphenyl, chlorophenyl, chloro and bromo.

3. A naphthopyran compound according to claim 1 which may be represented by one of the following graphic formulae:

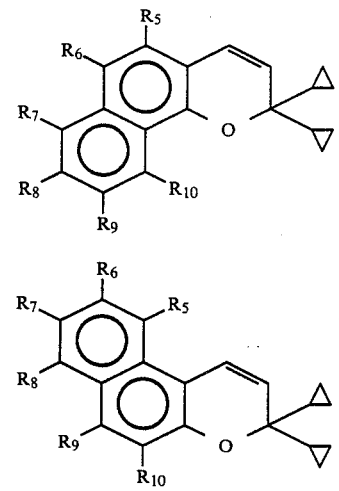

wherein $R_5$–$R_{10}$ are each selected from the group consisting of hydrogen, $C_1$–$C_3$ alkyl, $C_1$–$C_3$ alkoxy, chloro, bromo, phenyl, and $C_1$–$C_3$ alkoxyphenyl.

4. The compound of claim 3 wherein the naphthopyran is substituted only at the 5-position.

5. The compound of claim 3 wherein the naphthopyran is substituted only at the 5- and 6-positions.

6. The compound of claim 3 wherein the naphthopyran is substituted only at the 5- and 9-positions.

7. The compound of claim 4 wherein the $R_5$ substituent is selected from the group consisting of $C_1$–$C_3$ alkyl, $C_1$–$C_3$ alkoxy, $C_1$–$C_3$ alkoxyphenyl, chloro and bromo.

8. The compound of claim 5 wherein the $R_5$ and $R_6$ substituents are each selected from the group consisting of $C_1-C_3$ alkyl, $C_1-C_3$ alkoxy, $C_1-C_3$ alkoxyphenyl, chloro and bromo.

9. The compound of claim 6 wherein the $R_5$ and $R_9$ substituents are each selected from the group consisting of $C_1-C_3$ alkyl, $C_1-C_3$ alkoxy, $C_1-C_3$ alkoxyphenyl, chloro and bromo.

10. 5-methyl-9-methoxy-2,2-dicyclopropyl[2-H-1,2b]naphthopyran.

11. 5-methyl-2,2-dicyclopropyl[2-H-1,2b]naphthopyran.

12. A photochromic article comprising a solid transparent polymerized organic host material and a photochromic amount of a photochromic compound represented by one of the graphic formulae:

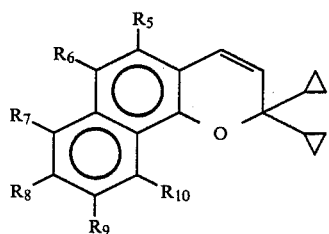

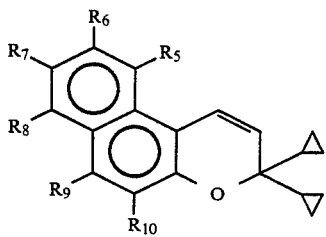

wherein $R_5-R_{10}$ are each selected from the group consisting of hydrogen, $C_1-C_3$ alkyl, $C_1-C_3$ alkoxy, chloro, bromo, phenyl, and $C_1-C_3$ alkoxyphenyl.

13. The photochromic article of claim 12 wherein the transparent polymerized organic host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

14. The photochromic article of claim 13 wherein the transparent polymerized organic host material is a homopolymer or copolymer of diethylene glycol bis(allyl carbonate).

15. The photochromic article of claim 14 wherein the photochromic compound is present in an amount of from 0.01 to 20 weight percent.

16. The photochromic article of claim 15 wherein the article is an optical element.

17. The photochromic article of claim 16 wherein the optical element is a lens.

18. A photochromic article comprising a solid transparent polymerized organic host material and a photochromic amount of each of (a) photochromic material selected from the group consisting of spiro(indolino) naphthoxazines and spiro(indolino) pyrido benzoxazines, and (b) photochromic material represented by one of the graphic formulae:

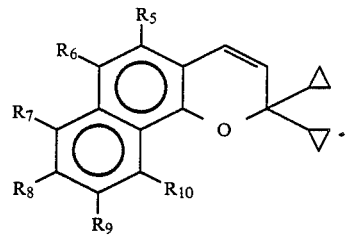

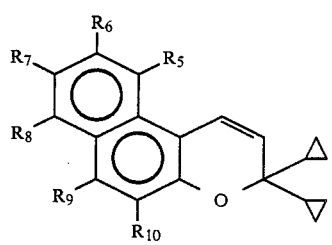

wherein $R_5-R_{10}$ are each selected from the group consisting of hydrogen, $C_1-C_5$ alkyl, $C_5-C_6$ cycloalkyl $C_1-C_3$ alkoxy, chloro, bromo, phenyl, $C_1-C_4$ alkoxyphenyl, $C_1-C_4$ alkylphenyl, and chlorophenyl, the mole ratio of photochromic material (a) to photochromic material (b) being from about 1:3 to about 3:1.

19. The photochromic article of claim 18 wherein the spiro(indolino) pyride benzoxazine is represented by the graphic formula:

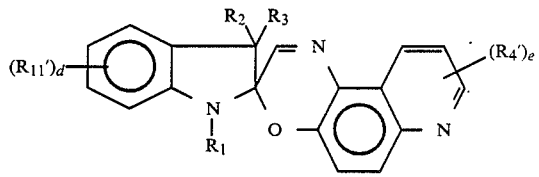

wherein,
(a) $R_1$ is selected from the group consisting of $C_1-C_4$ alkyl, phenyl, benzyl, 1-naphth($C_1-C_2$)alkyl, carboxy($C_2-C_4$)alkyl, cyano($C_2-C_4$)alkyl, $C_1-C_4$ acyloxy($C_2-C_4$)alkyl, hydroxy($C_2-C_4$)alkyl and $(C_2H_4O)_m.CH_3$, wherein m is an integer of from 1 to 3,
(b) $R_2$ and $R_3$ are each selected from the group consisting of $C_1-C_5$ alkyl and phenyl,
(c) $R_4$ is selected from the group consisting of $C_1-C_5$ alkyl, $C_1-C_5$ alkoxy and halogen, and the letter e is an integer of from 0 to 1,
(d) each $R_{11}$ is selected from the group consisting of $C_1-C_5$ alkyl, halogen, $C_1-C_5$ alkoxy, nitro, cyano, $C_1-C_4$ monohaloalkyl, $C_1-C_4$ polyhaloalkyl, $C_1-C_8$ alkoxycarbonyl and $C_1-C_4$ acyloxy, and the letter d is an integer of from 0 to 4.

20. The photochromic article of claim 18 wherein the spiro(indolino) naphthoxazine is represented by the graphic formula:

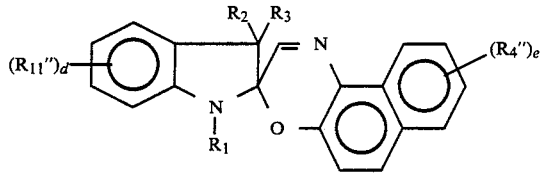

wherein,
(a) $R_1$ is selected from the group consisting of $C_1$–$C_4$ alkyl, phenyl, benzyl, 1-naphth($C_1$–$C_2$)alkyl, carboxy($C_2$–$C_4$)alkyl, cyano($C_2$–$C_4$)alkyl, $C_1$–$C_4$ acyloxy($C_2$–$C_4$)alkyl, hydroxy($C_2$–$C_4$)alkyl and $(C_2H_4O)_m\cdot CH_3$, wherein m is an integer of from 1 to 3,
(b) $R_2$ and $R_3$ are each selected from the group consisting of $C_1$–$C_5$ alkyl and phenyl,
(c) each $R''_4$ is selected from the group consisting of halogen, $C_1$–$C_5$ alkyl, $C_1$–$C_5$ alkoxy, nitro, cyano, thiocyano, $C_1$–$C_4$ monohaloalkyl, $C_1$–$C_2$ polyhaloalkyl, mono($C_1$–$C_4$)alkylamino and di($C_1$–$C_4$)alkylamino, and the letter e is an integer of from 0 to 2, and
(d) each $R'_{11}$ is selected from the group consisting of $C_1$–$C_5$ alkyl, halogen, $C_1$–$C_5$ alkoxy, nitro, cyano, $C_1$–$C_4$, monohaloalkyl, $C_1$–$C_4$ polyhaloalkyl, $C_1$–$C_8$ alkoxycarbonyl, $C_1$–$C_4$ acyloxy, and the letter d is a number of from 0 to 4.

21. The photochromic article of claim 18 wherein the transparent polymerized host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

22. The photochromic article of claim 19 wherein the transparent polymerized host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

23. The photochromic article of claim 21 wherein the host material is prepared from homopolymers and copolymers of diethylene glycol bis(allyl carbonate).

24. The photochromic article of claim 22 wherein the host material is prepared from homopolymers and copolymers of diethylene glycol bis(allyl carbonate).

25. The photochromic article of claim 23 wherein the photochromic compounds are each present in amounts of from about 0.05 to about 10 weight percent.

26. The photochromic article of claim 24 wherein the photochromic compounds are each present in amounts of from about 0.05 to about 10 weight percent.

27. The photochromic article of claim 25 wherein the photochromic article is an optical element.

28. The photochromic article of claim 26 wherein the photochromic article is an optical element.

29. The photochromic article of claim 25 wherein the ratio of the spiro(indolino) oxazine compound to the pyran compound varies from about 1:3 to about 3:1.

30. The photochromic article of claim 29 wherein the photochromic article is an ophthalmic lens.

31. The photochromic article of claim 28 wherein the ratio of the spiro(indolino) oxazine compound to the pyran compound varies from about 1:3 to about 3:1.

32. The photochromic article of claim 31 wherein the photochromic article is an ophthalmic lens.

* * * * *

UNITED STATES PATENT AND TRADEMARK OFFICE
CERTIFICATE OF CORRECTION

PATENT NO. : 4,931,221
DATED : June 5, 1990
INVENTOR(S) : Harry G. Heller, et al.

It is certified that error appears in the above-identified patent and that said Letters Patent is hereby corrected as shown below:

Claim 19, column 24, line 56, "$R_4$" should be --$R_4'$--

Claim 19, column 24, line 60, "$R_{11}$" should be --$R_{11}'$--

Claim 20, column 25, line 19, "$R''_4$" should be --$R_4''$--

Claim 20, column 25, line 26, "$R'_{11}$" should be --$R_{11}''$--

Claim 20, column 25, line 30, "a number" should be --an integer--

Signed and Sealed this

Fourth Day of February, 1992

Attest:

HARRY F. MANBECK, JR.

*Attesting Officer*        *Commissioner of Patents and Trademarks*